(12) United States Patent
Edwards et al.

(10) Patent No.: US 8,187,637 B2
(45) Date of Patent: May 29, 2012

(54) FORMULATIONS DECREASING PARTICLE EXHALATION

(75) Inventors: David A. Edwards, Boston, MA (US); Jonathan C. Man, Cambridge, MA (US); Jeffrey P. Katstra, Watertown, MA (US); Robert W. Clarke, Canton, MA (US)

(73) Assignee: Pulmatrix, Inc., Lexington, MA (US)

( * ) Notice: Subject to any disclaimer, the term of this patent is extended or adjusted under 35 U.S.C. 154(b) by 551 days.

(21) Appl. No.: 11/714,999

(22) Filed: Mar. 6, 2007

(65) Prior Publication Data

US 2007/0270502 A1    Nov. 22, 2007

Related U.S. Application Data

(62) Division of application No. 10/990,996, filed on Nov. 17, 2004, now abandoned.

(60) Provisional application No. 60/550,601, filed on Mar. 5, 2004, provisional application No. 60/560,470, filed on Apr. 7, 2004, provisional application No. 60/564,189, filed on Apr. 21, 2004, provisional application No. 60/572,631, filed on May 19, 2004, provisional application No. 60/579,425, filed on Jun. 14, 2004.

(51) Int. Cl.
*A61K 9/00* (2006.01)
*A61K 9/08* (2006.01)
*A61K 9/10* (2006.01)
*A61K 9/12* (2006.01)
*A61K 9/14* (2006.01)

(52) U.S. Cl. .......................................... 424/489; 424/46
(58) Field of Classification Search ................ 424/45, 424/46, 489
See application file for complete search history.

(56) References Cited

U.S. PATENT DOCUMENTS

| | | | |
|---|---|---|---|
| 4,828,844 A | 5/1989 | Rontgen-Odenthal et al. | |
| 5,175,152 A | 12/1992 | Singh | |
| 5,230,884 A | 7/1993 | Evans et al. | |
| 5,466,680 A | 11/1995 | Rudy | |
| 5,633,003 A | 5/1997 | Cantor | |
| 5,654,007 A | 8/1997 | Johnson et al. | |
| 5,709,202 A | 1/1998 | Lloyd et al. | |
| 5,855,913 A | 1/1999 | Hanes et al. | |
| 5,883,084 A | 3/1999 | Peterson et al. | |
| 5,985,309 A | 11/1999 | Edwards et al. | |
| 6,083,922 A | 7/2000 | Montgomery | |
| 6,083,933 A | 7/2000 | Montgomery | |
| RE37,053 E | 2/2001 | Edwards et al. | |
| 6,214,536 B1 | 4/2001 | Boucher | |
| 6,451,352 B1 | 9/2002 | Yvin et al. | |
| 2001/0008632 A1 | 7/2001 | Freund et al. | |
| 2002/0177562 A1 | 11/2002 | Weickert et al. | |
| 2003/0138403 A1* | 7/2003 | Drustrup ............... | 424/85.4 |
| 2004/0009128 A1 | 1/2004 | Rabinowitz et al. | |
| 2006/0142208 A1 | 6/2006 | Boucher | |
| 2007/0053844 A1 | 3/2007 | Watanabe et al. | |
| 2007/0270502 A1 | 11/2007 | Edwards et al. | |
| 2007/0275091 A1 | 11/2007 | King et al. | |
| 2008/0038207 A1 | 2/2008 | Edwards et al. | |

FOREIGN PATENT DOCUMENTS

| | | |
|---|---|---|
| EP | 0 367 723 | 5/1990 |
| EP | 0652011 | 5/1995 |
| WO | WO 92/06695 | 4/1992 |
| WO | WO 96/12470 | 5/1996 |
| WO | WO 97/36574 | 10/1997 |
| WO | WO 97/44013 | 11/1997 |
| WO | WO 99/64014 | 12/1999 |
| WO | WO 02/09574 | 2/2002 |
| WO | WO 03/092654 | 11/2003 |
| WO | WO03/092654 | 11/2003 |
| WO | WO 2006/102438 A2 | 9/2006 |

OTHER PUBLICATIONS

Shigeta et al. "Synergistic Anti-Influenza Virus A (H1N1) Activities of PM-523 (Polyoxometalate) and Ribavarin In Vitro and In Vivo," Antimicrobial Agents & Chemotherapy, 1997, 41, pp. 1423-1427.*
Tsurumi et al. "Effect of high salt treatment on influenza B viral protein synthesis in MDCK cells," Microbiology and Immunology, 1983, 27(6), pp. 519-529.*
Watanabe et al. "Why Inhaling Salt Water Changes What We Exhale," Journal of Colloid and Interface Science, 2007, 307, pp. 71-78.*
Fiegel et al., "Airborne Infectious Disease and the Suppression of Pulmonary Bioaerosols," DDT, Jan. 2006, 11(1/2), pp. 51-57.*
Edwards et al., "Inhaling to Mitigage Exhaled Bioaerosols," Proceedings of the National Academy of Sciences of the USA, Dec. 2004, 101(50), pp. 17383-17388.*
Sarrell et al., "Nebulized 3% Hypertonic Saline Solution Treatment in Ambulatory Children with Viral Bronchiolitis Decreases Symptoms," Chest, 2002, 122, pp. 2015-2020.*
Wade , C. E., "Hypertonic saline resuscitation in sepsis," Critical Care, Oct. 2002, 6(5), 397-398.*
Tsurumi et al. "Effect of high salt treatment on influenza B viral protein synthesis in MDCK cells," Microbiology and Immunology, 1983, 27(6), pp. 519-529 (Full document).*
The Online Merck Manual Medical Second Home edition article, entitled, "Influenza"-accessed on Feb. 22, 2010 at www.merck.com/mmhe/print/sec17/ch198/ch198d.html.*

(Continued)

Primary Examiner — James H. Alstrum-Acevedo
(74) Attorney, Agent, or Firm — McDermott Will & Emery LLP

(57) ABSTRACT

Formulations have been developed for pulmonary delivery to treat or reduce the infectivity of diseases such as viral infections, especially tuberculosis, SARS, influenza and respiratory synticial virus in humans and hoof and mouth disease in animals, or to reduce the symptoms of allergy or other pulmonary disease. Formulations for pulmonary administration include a material that significantly alters physical properties such as surface tension and surface elasticity of lung mucus lining fluid, which may be isotonic saline and, optionally, a carrier. The formulation may be administered as a liquid solution, suspension, aerosol, or powder where the particles consist basically of an osmotically active solute. Drugs, especially antivirals or antibiotics, may optionally be included with the formulation. These may be administered with or incorporated into the formulation.

43 Claims, 7 Drawing Sheets

OTHER PUBLICATIONS

Asthma: Lung and Airway Disorders, Merck Manual Home Edition, accessed at www.merck.com/mmhe/print/sec04/ch044/ch044a/html accessed on May 5, 2010.*

Chronic Obstructive Pulmonary Disease, Merck Manual Home Edition, accessed at www.merck.com/mmhe/print/sec04/ch045/ch045a/html accessed on Mar. 21, 2010.*

"Acute Respiratory Distress Syndrome (ARDS)," Merck Manual Home Edition, accessed on Novemeber 17, 2011 at www.merckmanuals.com/home/lung_and_airway_disorders/respiratory_failure_and_acute_respiratory_distress_syndrome/acute_respiratory_distress_syndrome_ards. html#v727948.*

Makker et al. "Relation of hypertonic saline responsiveness of the airways to exercise induced asthma symptom severity and to histamine or methacholine reactivity," Thorax, 1993, 48, pp. 142-147.*

Mai, X.-M. et al. "Hypertonic saline challenge tests in the diagnosis of bronchial hyperresponsiveness and asthma in children," Pediatric Allergy & Immunology, Oct. 2002, 13(5), pp. 361-367.*

Rodwell et al., "The effect of inhaled frusemide on airway sensitivity to inhaled 4.5% sodium chloride aerosol in asthmatic subjects," Thorax (1993) 48:208-213.

Adjei and Garren, "Pulmonary delivery of peptide drugs: Effect of particle size on bioavailability of leuprolide acetate in healthy male volunteers" *Pharm. Res.*, 7: 565-569 (1990).

Anderson, et al., "Effect of cystic fibrosis on inhaled aerosol boluses" *Am. Rev. Respir. Dis.*, 140: 1317-1324 (1989).

Bergeron, et al., "Controlling droplet deposition with polymer additives" *Nature*. 405:772-775 (2000).

Boren, "The development of a molecular model of lung" *Arch Intern Med* 126(3):491-495) (1970).

Choi, et al., "Inhalation delivery of proteins from ethanol suspensions" *Proc. Natl. Acad. Sci.* 98:11103-11107 (2001).

Clarke, et al., "Resistance to two-phase gas-liquid flow in airways" *J. Appl. Physiol.* 29(4): 464-471(1970).

Edwards, "The macrotransport of aerosol particles in the lung: aerosol deposition phenomena" *J. Aerosol Sci.*, 26:293-317 (1995).

Evrensel, et al., "Viscous airflow through a rigid tube with a compliant lining: A simple model for the air-mucus interaction in pulmonary pathways"*J. Biomech. Eng.* 115:262-27 (1993).

Ferguson, et al., "Transmission intensity and impact of control policies on the foot and mount epidemic in Great Britain" *Nature*, 414(6861): 329 (2001).

French, et al., "The influence of formulation on emission, deaggregation and deposition of dry powders for inhalation" *J. Aerosol Sci.*, 27: 769-783 (1996).

Gad-El-Hak, et al., "On the interaction of compliant coatins with boundary-layer flows" *J. Fluid Mech.*, 140: 257-280 (1984).

Ganderton, "The generation of respirable clouds form coarse powder aggregates" *Journal of Biopharmaceutical Sciences*, 3(1/2):101-10 5 (1992).

Gonda, "Aerosols for delivery of therapeutic and diagnostic agents to the respiratory tract," *Critical Reviews in Therapeutic Drug Carrier Systems*, 6:273-313 (1990).

Heyder J. et al., "Deposition of particles in the human respiratory tract in the size range 0.005-15μm" *J. Aerosol Sci.*, 17: 811-825 (1986).

Hirschman, et al., "Inhibition of human immunodeficiency virus type 1 replication by nonionic block polymer surfactants" *J Med Virol*. 42(3):249-54 (1994).

King, et al., "The effect of structured and unstructured pre-operative teaching: a replication" *Nurs. Res.* 31(6):324-9 (1982).

King, et al., "The role of mucus gel viscosity, spinnability, and adhesive properties in clearance by simulated cough" *Biorheology*, 26:737-745 (1989).

King, "Rheology of cystic fibrosis sputum after in vitro treatment with hypertonic saline alone and in combination with recombinant human deoxyribonuclease I" *Am. J. Respir. Crit. Care Med.*, 156(1):173-7 (1997).

Kurashima, et al., "A pilot study of surfactant inhalation for the treatment of asthmatic attack" *Arerugi*, 40(2):160-3 (1991).

Papineni and Rosenthal, "The size distribution of droplets in the exhaled breath of healthy human subjects" *J. Aerosol Med.*, 10(2): 105-116 (1997).

Patton and Platz, "Pulmonary delivery of peptides and proteins for systemic action" *Adv. Drug Del. Rev.*, 8:179-196 (1992).

Piret, et al., "Sodium lauryl sulfate, a microbicide effective against enveloped and nonenveloped viruses" *Curr. Drug Targets*. 3(1):17-30 (2002).

Rudt and Muller, "In vitro phagocytosis assay of nano- and microparticles by chemiluminescence. I. Effect of analytical parameters, particle size and particle concentration" *J. Controlled Release*, 22: 263-272 (1992).

Tabata and Ikada, 'Macrophage phagocytosis of biodegradable microspheres composed of L-lactic acid/glycolic acid homo- and copolymers *J. Biomed. Mater. Res.*, 22: 837-858 (1988).

Takebayashi, et al., "Role of tachykinins in airway responses to ozone in rats" *J Appl Physiol* 85: 442-450 (1998).

Tansey, "The challenges in the development of metered dose inhalation aerosols using ozone-friendly propellants" *Spray Technol. Market*. 4: 26-29 (1994).

Tibby, et al. "Exogenous surfactant supplementation in infants with respiratory syncytial virus bronchiolitis" *Am J Respir Crit Care Med.*, 162(4 Pt 1): 1251 (2000).

Timsina, et al., Drug delivery to the respiratory tract using dry powder inhalers *Int. J. Pharm.*, 101: 1-13 (1995).

Visser, "An invited review Vander Waals and other cohesive forces affecting powder fluidization" *Powder Technology*, 58: 1-10 (1989).

Vollenbroich, et al., "Mechanism of inactivation of enveloped viruses by the biosurfactant surfactin from *Bacillus subtilis* " *Biologicals*, 25(3):289-97 (1997).

Wanatabe, et al., "Immunogenicity and protective efficacy of replication-incompetent influenza virus-like particles" *Journal of Virology* 76(2):767-773 (2002).

Zanen and Lamm, 'The optimal particle size for parasympathicolytic aerosols in mild asthmatics *J. Int J. Pharm.*, 114: 111-115 (1995).

Rote Liste Service: "Rote Liste 2002", Editio Cantor Verlag, Aulendorf (2002).

Adjei and Garren, "*Pulmonary delivery of peptide drugs: Effect of particle size on bioavailability of leuprolide acetate in healthy male volunteers*", Pharm. Res. 7:565-569 (1990).

Anderson, et al., "*Effect of cystic fibrosis on inhaled aerosol boluses*", Am. Rev. Respir. Dis., 140:1317-1324 (1989).

Bergeron, et al., "*Controlling droplet deposition with polymer additives*", Nature, 405:772-775 (2000).

Boren, "*The development of a molecular model of lung*", Arch. Intern. Med. 126(3):491-495 (1970).

Choi, et al., "*Inhalation deliver of proteins from ethanol suspensions*", Proc. Natl. Acad. Sci. 98:11103-11107 (2001).

Clarke, et al., "*Resistance to two-phase gas-liquid flow in airways*", J. Appl. Physiol. 29(4):464-471 (1970).

Edwards, "*The macrotransport of aerosol particles in the lung: aerosol deposition phenomena*", J. Aerosol Sci., 26:293-317 (1995).

Evrensel, et al., "*Viscous airflow through a rigid tube with a compliant lining: A simple model for the air-mucus interaction in pulmonary pathways*", J. Biomech. Eng. 115:262-27 (1993).

Ferguson, et al., "*Transmission intensity and impact of control policies on the foot and mount epidemic in Great Britain*", Nature, 414(6861):329 (2001).

French, et al., "*The influence of formulation on emission, deaggregation and deposition of dry powders for inhalation*", J. Aerosol Sci., 27:769-783 (1996).

Gad-El-Hak, et al., "*On the interaction of compliant coatins with boundary-layer flows*", J. Fluid Mech., 140:257-280 (1984).

Ganderton, "*The generation of respirable clouds form coarse powder aggregates*", Journal of Biopharmaceutical Sciences, 3(1/2):101-105 (1992).

Gonda, "*Aerosols for delivery of therapeutic and diagnostic agents to the respiratory tract*", Critical Reviews in Therapeutic Drug Carrier Systems, 6:273-313 (1990).

Heyder J., et al., "*Deposition of particles in the human respiratory tract in the size range 0.005-15μm*", J. Aerosol Sci., 17:811-825 (1986).

Hirschman, et al., "*Inhibition of human immunodeficiency virus type 1 replication by nonionic block polymer surfactants*", J. Med. Virol. 42(3):249-54 (1994).

King, et al., "The effect of structured and unstructured pre-operative teaching: a replication", Nurs. Res. 31(6):324-9 (1982).

King, et al., "The role of mucus gel viscosity, spinnability, and adhesive properties in clearance by simulated cough", Biorheology, 26:737-745 (1989).

King, "Rheology of cystic fibrosis sputum after in vitro treatment with hypertonic saline alone and in combination with recombinant human deoxyribonuclease I", Am. J. Respir. Crit. Care Med., 156(1):173-7 (1997).

Kurashima, et al., "A pilot study of surfactant inhalation for the treatment of asthmatic attack", Arerugi, 40(2):160-3 (1991).

Papineni and Rosenthal, "The size distribution of droplets in the exhaled breath of healthy human subjects", J. Aerosol Med., 10(2)105-116 (1997).

Patton and Platz, "Pulmonary delivery of peptides and proteins for systemic action", Adv. Drug Del. Rev., 8:179-196 (1992).

Piret, et al., "Sodium lauryl sulfate, a microbicide effective against enveloped and nonenveloped viruses", Curr. Drug Targets, 3(1):17-30 (2002).

Rudt and Muller, "In vitro phagocytosis assay of nano- and microparticles by chemiluminescence. I. Effect of analytical parameters, particle size and particle concentration", J. Controlled Release, 22:263-272 (1992).

Tabata and Ikada, "Macrophage phagocytosis of biodegradable microspheres composed of L-lactic acid/glycolic acid homo- and copolymers", J. Biomed. Mater. Res., 22:837-858 (1988).

Takebayashi, et al., "Role of tachykinins in airway responses to ozone in rats", J. App. Physiol. 85:442-450 (1998).

Tansey, "The challenges in the development of metered dose inhalation aerosols using ozone-friendly propellants", Spray Technol. Market, 4:26-29 (1994).

Tibby, et al., "Exogenous surfactant supplementation in infants with respiratory syncytial virus bronchiolitis", Am. J. Respir. Crit. Care Med., 162(4 Pt 1):1251 (2000).

Timsina, et al., "Drug delivery to the respiratory tract using dry powder inhalers", Int. J. Pharm., 101:1-13 (1995).

Visser, "An invited review Vander Waals and other cohesive forces affecting powder fluidization", Powder Technolgoy, 58:1-10 (1989).

Vollenbroich, et al., "Mechanism of inactivation of enveloped viruses by the biosurfactant surfactin from Bacillus subtilis", Biologicals, 25(3):289-97 (1997).

Wanatabe, et al., "Immunogenicity and protective efficacy of replication-incompetent influenza virus-like particles", Journal of Virology 76(2):767-773 (2002).

Zanen and Lamm, "The optimal particle size for parasympathicolytic aerosols in mild asthmatics", J. Int. J. Phar., 114:111-115 (1995).
Hawley's Condensed Chemical Dictionary, 14th edition, John Wiley & Sons, Inc., 2001, pp. 161 and 977.
Cataldo, et al., "*Induced sputum: comparison between isotonic and hypertonic saline solution inhalation in patients with asthma*", Chest, 120(6):1815-21 (2001).
Copp, et al., "*Hypertonic Shock Inhibits Growth Factor Receptor Signaling, Induces Caspase-3 Activation, and Causes Reversible Fragmentation of the Mitochondrial Network*," Am. J. Physiol, 288:C403-C415 (2005).
Guo-Zhong Tao, et al., "*Hyposmotic Stress Induces Cell Growth Arrest Via Proteasome Activation and Cyclin/Cyclin-Dependent Kinase Degradation*,"J. Biological Chemistry, 277(22): 19295-19303 (2002).
Burg, et al., "*Cellular Response to Hyperosmotic Stresses*," Am. Physiological Soc., 87:1441-1474 (2007).
Marriott, et al., "*Changes in the Gel Properties of Tracheal Mucus Induced by Divalent Cations*," Biorheology, 1979, pp. 331-337, vol. 16.
Suara, et al. "*Effect of Zinc Salts on Respiratory Syncytial Virus Replication*,"Antimicrobial Agents and Chemotherapy, Mar. 2004, pp. 783-790, vol. 48 (3).
Friedman, et al. "*A Randomized, Prospective, Double-Blind Study on the Efficacy of Dead Sea Salt Nasal Irrigations*,"The Laryngoscope, 2006, pp. 878-882, 116.
King, et al. "*Mucomodulator Therapy in Cystic Fibrosis: Balancing Mucus Clearability Against the Spread of Airborne Pathogens*," Pediatric Pulmonology, 2004, pp. 77-79, Supp. 26.
Raynal, et al. "*Calcium-dependent Protein Interactions in MUC5B Provide Reversible Cross-links in Salivary Mucus*," The Journal of Biological Chemistry, Aug. 2003, pp. 28703-28710, vol. 278 (31).
Aldrich Chemical Catalog, 1998-1999, p. 1502.
Bromberg and Klibanov, "Transport of proteins dissolved in organic solvents across biomimetic membranes", *Proc. Natl. Acad. Sci. USA*, 92(5):1262-6 (1995).
Fuge, et al., "The geochemistry of iodine-a review", *Environmental Geochemistry and Health*, 8(2):31-54 (1986).
Hardy, et al., "Sensitivity of aerosol bolus behavior to methacholine-induced bronchoconstriction", *Chest*, 114(2):404-10 (1998).
Iwasaki, et al., "Exacerbation of influenzavirus pneumonia by intranasal administration of surfactant in a mouse model", *Arch. Virol.*, 144:675-685 (1999).
King, "Rheology of cystic fibrosis sputum after in vitro treatment with hypertonic saline alone and in combination with recombinant human deoxyribonuclease I", *Am. J. Respire. Crit. Care Med.*, 156(1):173-7 (1997).
Lipp, et al., "Solving medical problems with chemical engineering", *Chemtech*, 42-57 (Mar. 1997).
Nanaumi, et al., "Properties of mixed monolayers of DPCC and viscoelasticity-giving substances", *Colloids & Surfaces B: Bioinformatics*, 17:167-174 (2000).
Rosenblum, "fish", Grolier Multimedia Encyclopedia, 2006, Grolier Online, accessed Nov. 21, 2006 (gme.grolier.com/cgi-bin/article?assetid=0106750-0).
The Merck Index, $12^{th}$ Edition, Merck & Co., Inc., Whitehouse Station, NJ, 1996, pp. 177 & 1614-1615.
Wikipedia, "Hypertonic" Wikipedia, 2006, accessed Nov. 21, 2006 (en.wikipedia.org/wiki/Hypertonic).
Zasadzinski, et al., "The physics and physiology of lung surfactants", *Current Opinion in Colloid & Interface Science*, 6:506-513 (2001).
Eng PA, et al., "Short-term efficacy of ultrasonically nebulized hypertonic saline in cystic fibrosis," *Pediatr. Pulmonol.*, 21:77-83 (1996).
Riedler, J., et al., "Inhaled hypertonic saline increases sputum expectoration in cystic fibrosis," *J. Pediatr Child Health*, 32:48-50 (1996).
Robinson, M., et al., "Effect of hypertonic saline, amiloride, and cough on mucociliary clearance in patients with cystic fibrosis," *Am. J. Respir. Crit. Care Med.*, 153:1503-1509 (1996).
Robinson, M., et al., "Effect of increasing doses of hypertonic saline on mucociliary clearance in patients with cystic fibrosis," *Thorax*, 52:900-903 (1997).
Robinson, M., et al., "The effect of inhaled mannitol on bronchial mucus clearance in cystic fibrosis patients: a pilot study," *Eur. Respir. J.*, 14:678-685 (1999).
King, M., et al., "Rheology of cystic fibrosis sputum after in vitro treatment with hypertonic saline alone and in combination with recombinant human deoxyribonuclease I," *Am. J. Respir. Crit. Care Med.*, 156:173-177 (1997).

* cited by examiner

FIG. 1

Air Source → Valve → Flow Restrictor → Model Trachea (with Pressure Transducer, Mucus Mimetic (green), ALPM Material (blue)) → To Aerosol Characterization

FIG. 2

Real Cough: V̇ (1/s), 0.5 s

Simulated Cough (5psi tank pressure): Flow Rate (L/s) vs Time (s)

Cough Distribution at 0 Minutes
$x_{10} = 0.28\ \mu m$   $x_{20} = 0.42\ \mu m$   $x_{30} = 0.66\ \mu m$ Cough Distribution at 0 Minutes (Post Dose)
$x_{10} = 0.51\ \mu m$   $x_{20} = 1.00\ \mu m$   $x_{30} = 1.67\ \mu m$ Cough Distribution at 30 Minutes
$x_{10} = 0.27$ μm    $x_{20} = 0.35$ μm    $x_{30} = 0.44$ μm Cough Distribution at 30 Minutes (Post Dose)
$x_{10} = 47.89$ μm    $x_{20} = 61.94$ μm    $x_{30} = 71.19$ μm Cough Distribution at 60 Minutes
$x_{10} = 0.27$ μm   $x_{20} = 0.35$ μm   $x_{30} = 0.44$ μm Cough Distribution at 60 Minutes (Post Dose)
$x_{10} = 25.58$ μm   $x_{20} = 31.71$ μm   $x_{30} = 36.90$ μm Baseline Particle Counts by Subject Pre-Dosing with Prototype Formulation 2 n=11

Patients w/Baseline >1,000 Particles/Liter
n=2

Patients w/Baseline >1,000 Particles/Liter
Formulation 1 (n=2): Formulation 2 (n=5)

Sham Exposure Particle Counts (N=7)

% Baseline Dose Data (n=6.7)

FORMULATIONS DECREASING PARTICLE EXHALATION

CROSS-REFERENCE TO RELATED APPLICATIONS

This application is a divisional of U.S. application Ser. No. 10/990,996, filed Nov. 17, 2004, now abandoned which in turn claims priority from U.S. provisional application Ser. No. 60/579,425, filed Jun. 14, 2004; U.S. provisional application Ser. No. 60/572,631, filed May 19, 2004; U.S. provisional application Ser. No. 60/564,189, filed Apr. 21, 2004; U.S. provisional application Ser. No. 60/560,470, filed Apr. 7, 2004; and U.S. provisional application Ser. No. 60/550,601, filed Mar. 5, 2004.

FIELD OF THE INVENTION

The present invention is in the field of formulations and systems to decrease the incidence of bioaerosol exhalation.

BACKGROUND OF THE INVENTION

Viral and bacterial infections are frequently highly contagious, especially when spread by respiration. The recent reports regarding Severe Acute Respiratory Syndrome ("SARS"), now known to be caused by a corona virus, are proof of how rapidly an infection can spread when it is transmitted through air contact. Other diseases such as influenza spread by air contact, and rapidly reach epidemic proportions, with high numbers of fatalities in elderly and immunocompromised populations.

SARS is a respiratory illness that has recently been reported in Asia, North America, and Europe. As of Apr. 20, 2003, about 198 suspect cases of SARS and 38 probable cases of SARS had been reported in the United States. In general, SARS begins with a fever greater than 100.4° F. [>38.0° C.]. Other symptoms may include headache, an overall feeling of discomfort, and body aches. Some people also experience mild respiratory symptoms. After 2 to 7 days, SARS patients may develop a dry cough and have trouble breathing.

SARS appears to spread primarily by close person-to-person contact. Most SARS cases have involved people who cared for or lived with someone with SARS, or had direct contact with infectious material (for example, respiratory secretions) from a person who has SARS. Potential ways in which SARS can be spread include touching the skin of other people or objects that are contaminated with infectious droplets and then touching your eye(s), nose, or mouth. This can happen when someone who is sick with SARS coughs or sneezes droplets onto themselves, other people, or nearby surfaces. It is also possible that SARS can be spread more broadly through the air or by other ways that are currently not known. At present there is no treatment or means of prevention for SARS, other than supportive care.

TB, or tuberculosis, is a disease caused by the bacteria *Mycobacterium tuberculosis*. The bacteria can attack any part of the body, but usually attacks the lungs. TB was once the leading cause of death in the United States. In the 1940s, scientists discovered the first of several drugs now used to treat TB. As a result, TB slowly began to disappear in the United States. Recently, TB has made a resurgence. Between 1985 and 1992, the number of TB cases increased, with more than 16,000 cases reported in the United States in 2000 alone.

TB is spread through the air from one person to another. The bacteria are dispersed into the air when a person with TB of the lungs or throat coughs or sneezes. People nearby may breathe in these bacteria and become infected. When a person breathes in *Mycobacterium tuberculosis*, the bacteria can settle in the lungs and begin to grow. From there, it can spread through the blood to other parts of the body, such as the kidney, spine, and brain. People with TB are most likely to spread it to people they come in contact with on a daily basis. People who are infected with latent TB do not feel sick, are asymptomatic, and cannot spread TB, but they may develop TB at some time in the future.

Bacteria are not the only sources of infectious diseases. Viruses are also highly contagious and have no effective treatments other than containment. For example, Respiratory syncytial virus (RSV) is a very common virus that causes mild cold-like symptoms in adults and older healthy children. By age two, nearly all infants have been infected by RSV. RSV can cause severe respiratory infections in infants, particularly those born prematurely, with heart or lung disease, or immunocompromised. Seasonal outbreaks of acute respiratory illness typically occur in the fall and last into the spring. RSV is spread easily by physical contact. Transmission is usually by contact with contaminated secretions, called foamites, which may involve tiny droplets or objects that droplets have touched. RSV can live for half an hour or more on human hands. The virus can also live up to five hours on countertops and for several hours on used tissues. RSV often spreads very rapidly in crowded households and day care centers. Each year up to 125,000 infants are hospitalized due to severe RSV disease, and about 1-2% of these infants die. It has been reported that exogenous surfactant supplementation in infants with respiratory syncytial virus bronchiolitis was beneficial (Tibby, et al. Am J Respir Crit Care Med October 2000; 162(4 Pt 1):1251). The principle means of treatment remains supportive however, and there is no means of limiting spread other than isolation.

Influenza is another common viral infection for which there is no effective treatment, and containment is the only option to limit spread of disease. Influenza is caused by three viruses—Influenza A, B and C. Type A is usually responsible for large outbreaks and is most adept at mutating. New strains of Type A virus develop regularly and cause new epidemics every few years. Type B causes smaller outbreaks, and Type C usually causes mild illness. In the United States, infection with influenza A and B leads to 20,000 deaths and over 100,000 hospitalizations each year. Influenza is transmitted person to person via contagious droplets that are formed when someone sneezes or coughs.

Approximately 8 million children and adolescents between 6 months and 17 years of age have one or more medical conditions that put them at increased risk of influenza-related complications. Such children include those with chronic disorders of the heart or lungs (such as asthma and cystic fibrosis), children who have required regular medical follow-up or hospitalization during the preceding year because of chronic metabolic diseases (including diabetes mellitus), kidney dysfunction, sickle cell anemia, or immunosuppression.

For unvaccinated individuals who have been exposed to people with known influenza, especially if the exposed individual has risk factors, potential use of antiviral medication for more than 2 weeks and vaccination may help prevent illness. For mild illness in people who are not at high-risk, the treatment of influenza is frequently just supportive and includes bed rest, analgesics for muscle aches and pains, and increased intake of fluids. Treatment is usually not necessary for children, but may be prescribed if the illness is diagnosed early and the patient is at risk of progression to more severe infection. Among individuals in high-risk groups (elderly, immunosuppressed, chronic heart, lung or kidney conditions) influenza may be quite severe and can lead to complications or death.

Epidemics of respiratory infections are not limited to humans. Foot-and-mouth disease virus (FMDV) is the etiologic agent of foot-and-mouth disease (FMD), which is a disease of cattle, swine, and other cloven-footed animals. FMD is characterized by the formation of vesicles on the tongue, nose, muzzle, and coronary bands of infected animals. Several unique characteristics make the virus one of the most economically devastating diseases in the world today. The ease with which it may be transmitted by contact and aerosol, combined with its enhanced ability to initiate infections, virtually ensures that most, if not all, animals in a herd will contract FMD. The long-term survival of FMDV in infected animals' tissues and organs, especially when refrigerated, offers an opportunity for its national and international transmission through the food chain. Multiple serotypes and numerous subtypes reduce the effectiveness and reliability of vaccines. The possible development of carriers in vaccinated animals and those that have recovered from FMD provides additional potential sources of new outbreaks. These features create a disease that can have a major economic impact on live stock operations around the world. The foot and mouth disease (FMD) epidemic in British livestock remains an ongoing cause for concern, with new cases still arising in previously unaffected areas (Ferguson, et al., Nature 2001 414(6861): 329). The parameter estimates obtained in a dynamic model of disease spreading show that extended culling programs were essential for controlling the epidemic to the extent achieved, but demonstrate that the epidemic could have been substantially reduced in scale had the most efficient methods been used earlier in the outbreak.

Viral shedding through bioaerosol exhalation is one mechanism, for infection transmission from a host leading to inhalation by another animal or human. The devastating consequences that uncontrolled viral shedding can have on livestock were seen in the hoof and mouth disease outbreak in the U.K., where 2030 confirmed cases resulted in the mandatory slaughter of 4 million animals. Recently, more attention is being given to the threat of bioterrorism and the similar risk that a sudden outbreak of disease poses to livestock in the U.S.

Airborne infection is one of the main routes of pathogen transmission. Aerosols composed of mucus droplets originating in the lungs and nasal cavities are produced when a human or animal coughs or simply breathes. These bioaerosols can contain pathogens that transmit the disease upon inhalation by exposed humans or animals. In addition, respirable pathogenic bioaerosols produced in the upper airways can be re-breathed by the host leading to parenchymal infection with exacerbated disease outcomes.

WO03/092654 to David Edwards et al. describes a method for diminishing the spread of inhaled infections by delivering materials such as surfactants that suppress bioaerosol expiration. This technique works on the basis of altering the surface or other physical properties of the endogenous surfactant fluid in the lungs, and thereby favoring fewer exhaled bio-aerosol particles. It would be desirable to have other means of limiting bioaerosol formation and/or spread.

It is therefore an object of the present invention to provide formulations for use in decreasing or limiting spread of pulmonary infections, especially viral or bacterial infections, without delivery of surfactant material to the lungs.

It is further an object of the present invention to provide a method of treatment to decrease or limit the spread of pulmonary infections to other animals or humans, especially viral or bacterial infections.

It is further an object of the present invention to provide a method of treatment to decrease or limit the spread of pulmonary infections, especially viral or bacterial infections, within a patient.

It is further an object of the present invention to provide formulations for treatment of humans or animals to limit infectivity.

It is yet a further object of this invention to manufacture a device for the measurement of exhaled particle number and particle size to diagnose those animals or humans, with an enhanced propensity to exhale aerosols.

SUMMARY OF THE INVENTION

Formulations have been developed for delivery by any route to reduce the infectivity of diseases such as viral infections, especially tuberculosis, SARS, influenza, cytomegalovirus and RSV in humans and hoof and mouth disease in animals. In one embodiment, the formulation for administration is a non-surfactant solution that, via dilution of endogenous surfactant fluid, alters physical properties such as surface tension, surface elasticity and bulk viscosity of lung mucus lining fluid. The aerosolized material may be an isotonic saline solution, a hypertonic saline solution or other solution containing osmotically active materials. The formulation may be administered as a powder where the particles consist essentially of a salt or osmotically-active substance that dilutes endogenous surfactant fluid. The aerosol may be a solution, suspension, spray, mist, vapor, droplets, particles, or a dry powder, for example, using a metered dose inhaler including HFA propellant, a metered dose inhaler with non-HFA propellant, a nebulizer, a pressurized can, or a continuous sprayer. The aerosol is preferably an aqueous solution, and more preferably isotonic saline, or it may contain a particularly effective osmotically-active substance, like mannitol. The formulation may be an organic suspension or solution for aerosol delivery. The formulation may be a vapor. Typical concentrations of salts or sugars are in the range of up to 5 or 6% solute. In a preferred embodiment, the formulations are administered either as a powder or aerosol, preferably prior to or shortly after infection, allergy or asthma attack. The formulations are administered to decrease or prevent exhalation of particulate matter, especially of infectious particulate matter. The formulation is administered in an amount sufficient to decrease surface instabilities in the liquid lining the airways of the lung, i.e., to damp the rate of droplet formation from lung fluid, without causing expectoration. Examples demonstrate suitable formulations and effective amounts. An example demonstrates efficacy of administration of nebulized saline over a period of up to twelve minutes, preferably two minutes or greater, to decrease particle exhalation in cattle.

A method of screening animals or humans for a number of characteristics, including the measurement of expired air and inspired air, the assessment of exhaled particle numbers, the assessment of exhaled particle size and the assessment of tidal volume and respiratory frequency during sampling, was devised to aid in the diagnosis of animals or humans who have an enhanced propensity to exhale aerosols. A device with sufficient sensitivity to accurately count sub-micron sized particles was designed and assembled. The device is portable and operates on batteries. Particle number and size can be determined by infrared spectroscopy, laser diffraction or light scattering.

BRIEF DESCRIPTION OF THE DRAWINGS

FIG. 1 is a diagram of the simulated cough machine apparatus.

FIG. 2 illustrates an actual cough profile versus a simulated cough profile.

DETAILED DESCRIPTION OF THE INVENTION

Figure 3A:
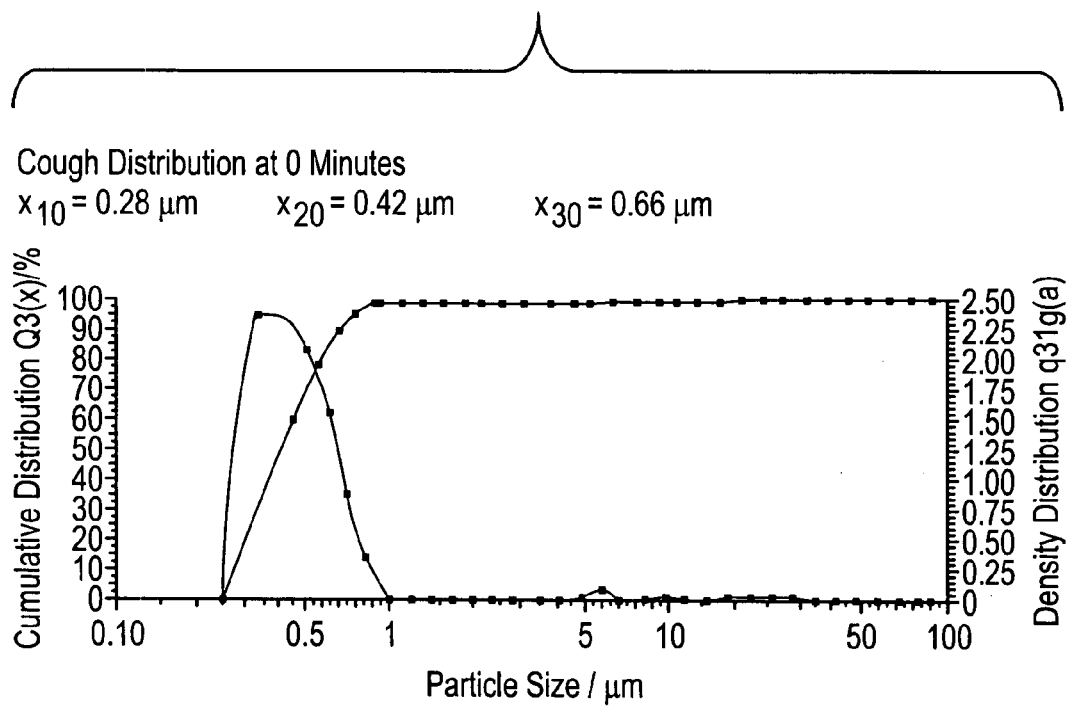
FIG. 3A, FIG. 3B, and FIG. 3C illustrate particle concentration following three coughs measured over time for plain mucus stimulant and following saline delivery at t=0 (FIG. 3A), t=30 (FIG. 3B) and t=60 (FIG. 3C) minutes.
Figure 3A:
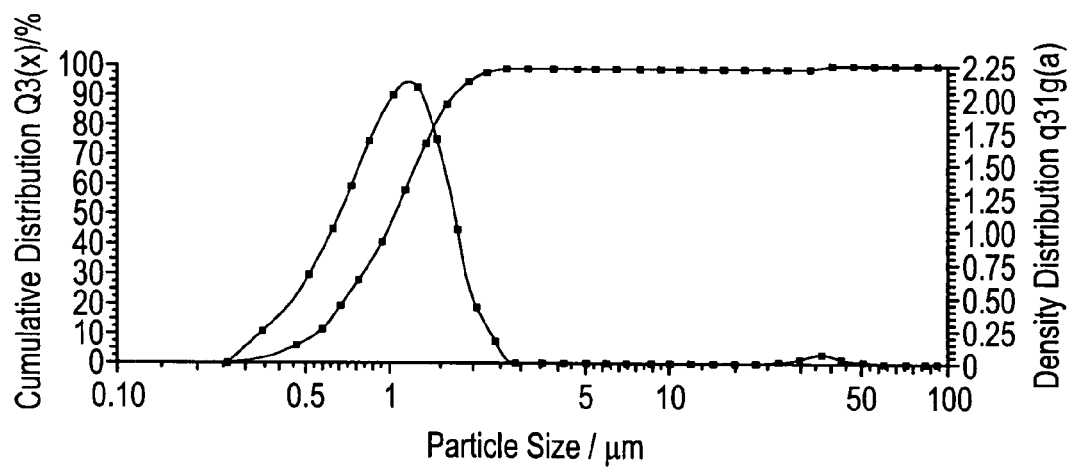
Figure 3B:
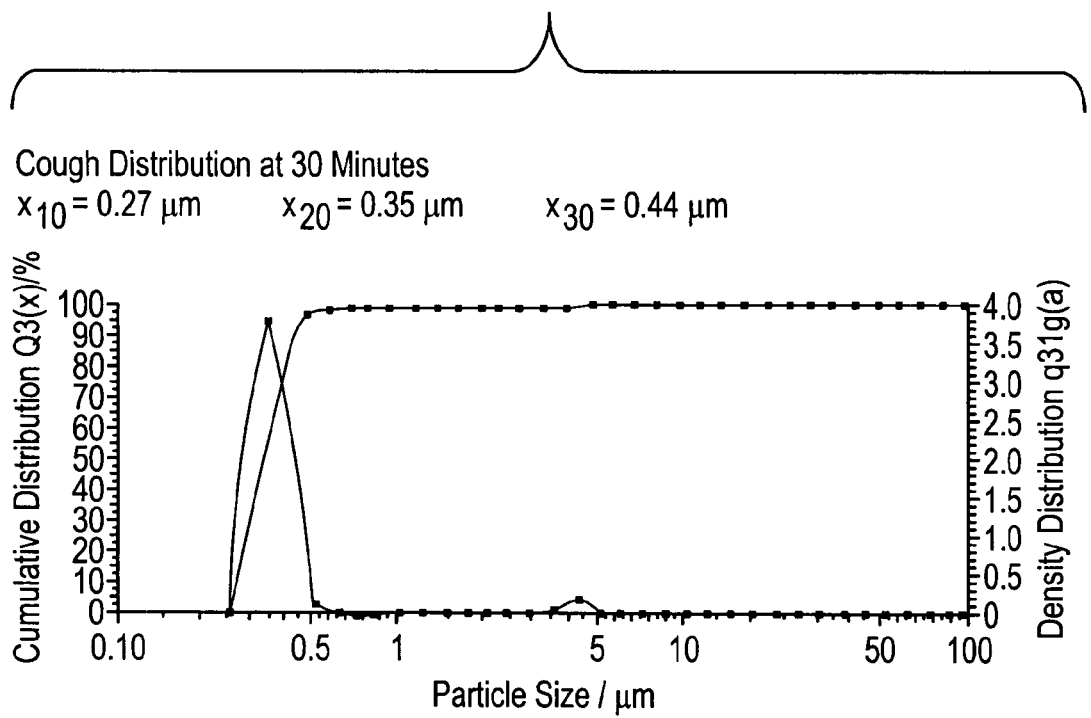
Figure 3B:
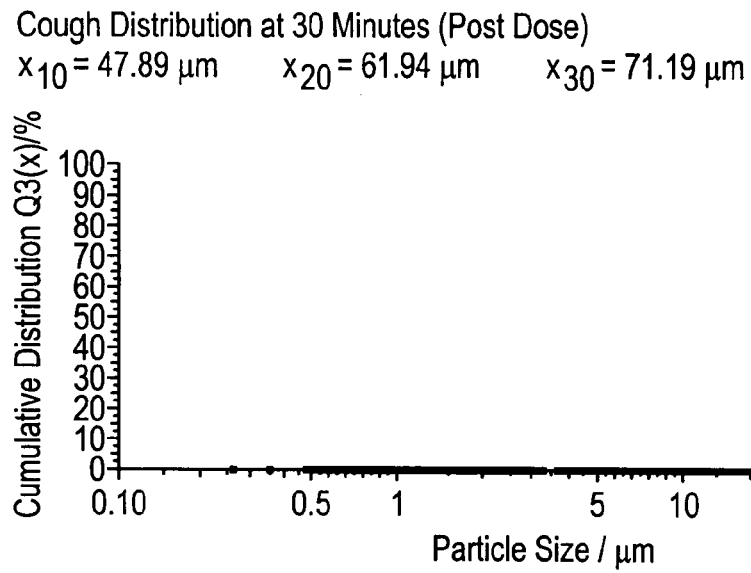
Figure 3C:
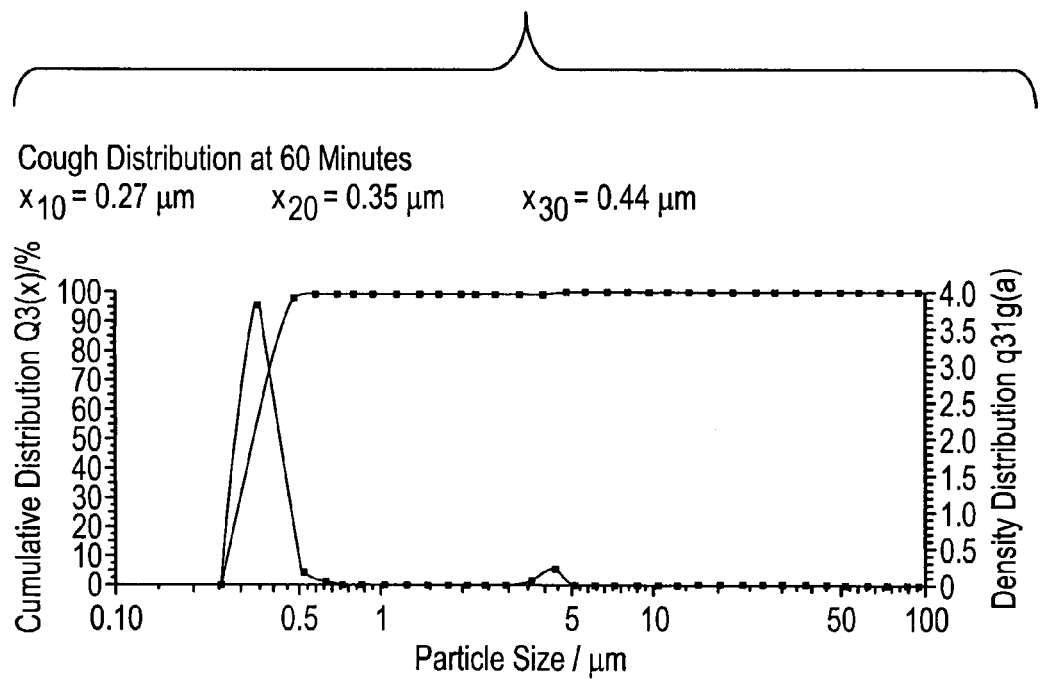
Figure 3C:
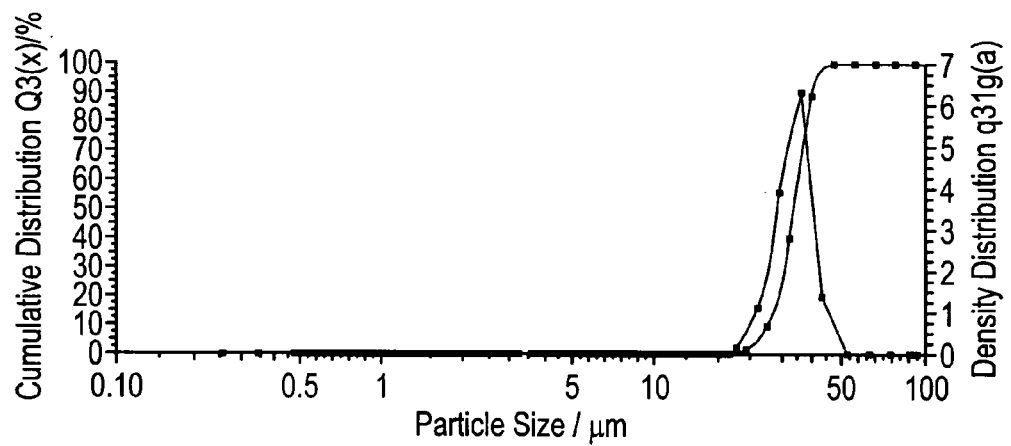

Lung mucociliary clearance is the primary mechanism by which the airways are kept clean from particles present in the liquid film that coats them. The conducting airways are lined with ciliated epithelium that beat to drive a layer of mucus towards the larynx, clearing the airways from the lowest ciliated region in 24 hours. The fluid coating consists of water, sugars, proteins, glycoproteins, and lipids. It is generated in the airway epithelium and the submucosal glands, and the thickness of the layer ranges from several microns in the trachea to approximately 1 micron in the distal airways in humans, rat, and guinea pig.

A second important mechanism for keeping the lungs clean is via momentum transfer from the air flowing through the lungs to the mucus coating. Coughing increases this momentum transfer and is used by the body to aid the removal of excess mucus. It becomes important when mucus cannot be adequately removed by ciliary beating alone, as occurs in mucus hypersecretion associated with many disease states. Air speeds as high as 200 m/s can be generated during a forceful cough. The onset of unstable sinusoidal disturbances at the mucus layer has been observed at such air speeds. This disturbance results in enhanced momentum transfer from the air to the mucus and consequently accelerates the rate of mucus clearance from the lungs. Experiments have shown that this disturbance is initiated when the air speed exceeds some critical value that is a function of film thickness, surface tension, and viscosity (M. Gad-El-Hák, R. F. Blackwelder, J. J. Riley. *J. Fluid Mech.*—(1984) 140:257-280). Theoretical predictions and experiments with mucus-like films suggest that the critical speed to initiate wave disturbances in the lungs is in the range of 5-30 m/s.

Papineni and Rosenthal (J. Aerosol Med., 1997, 10(2): 105-116) have demonstrated that during standard mouth and nose breathing, or during coughing, normal human subjects expire tens to hundreds of liquid bioaerosol droplets, with a preponderance of exhaled bioaerosol droplets having a diameter smaller than one micron. Coughing was shown to give rise to the greatest number of particles, although the mean exhaled particle size remained significantly less than a micron. The majority of these particles are larger than most inhaled pathogens, i.e., greater than 150 nm. For instance, some common inhaled pathogens have characteristic sizes in this range: tuberculosis, 1,000-5,000 nm; influenza, 80-120 nm; measles, 100-250 nm; chicken pox, 120-200 nm; FMD, 27-30 nm.

I. Formulations

Bioaerosol particles are formed by instabilities in the endogenous surfactant layer in the airways. This instability depends on endogenous surfactant concentration in the lungs. This surfactant concentration can be altered by simply diluting the endogenous surfactant pool via either delivery of isotonic saline (though not in such a large amount as to cause a subject to expectorate) or a hypertonic saline solution that causes the cells lining the lung's airways to dilute further the endogenous surfactant layer via production of water.

The formulations described herein are effective to decrease aerosol exhalation, by preventing or reducing exhaled particle formation from the oropharynx or nasal cavities. A preferred aerosol solution for altering physical properties of the lung's lining fluid is isotonic saline. Saline solutions have long been delivered chronically to the lungs with small amounts of therapeutically active agents, such as beta agonists, corticosteroids, or antibiotics. For example, VENTOLIN® Inhalation Solution (GSK) is an albuterol sulfate solution used in the chronic treatment of asthma and exercise-induced bronchospasm symptoms. A VENTOLIN® solution for nebulization is prepared (by the patient) by mixing 1.25-2.5 mg of albuterol sulfate (in 0.25-0.5 mL of aqueous solution) into sterile normal saline to achieve a total volume of 3 mL. No adverse effects are thought to be associated with the delivery of saline to the lungs by VENTOLIN® nebulization, even though nebulization times can range from 5-15 minutes. Saline is also delivered in more significant amounts to induce expectoration. Often these saline solutions are hypertonic (sodium chloride concentrations greater than 0.9%, often as high as 5%) and generally they are delivered for up to 20 minutes. Saline solutions can contain about 0.9% to 5% (w/w) NaCl. In some embodiments, the saline solution contains about 0.9% NaCl.

It has been discovered that physical properties of the endogenous surfactant fluid in the lungs, such as surface tension, can be altered by administration of a saline solution, as well as by administration of an aqueous saline solution containing other materials, such as surfactant.

The term "aerosol" as used herein refers to any preparation of a fine mist of particles, typically less than 10 microns in diameter, which can be in solution or a suspension. The preferred mean diameter for aqueous formulation aerosol particles is about 3 microns, for example between 0.1 and 30 microns, most preferably between 1 and 10 microns. The aerosol can consist just of a solution, such as an aqueous solution, most preferably a saline solution. Alternatively, the aerosol may consist of an aqueous suspension or dry particles. Concentration ranges of the salt or other osmotically active material range from about 0.01% to about 10% by weight, preferably between 0.9% to about 10%.

A. Osmotically Active Materials

Many materials may be osmotically active, including binary salts, such as sodium chloride, or any other kinds of salts, or sugars, such as mannitol. Osmotically active materials, normally owing to their ionization and possibly size, do not easily permeate cell membranes and therefore exert an osmotic pressure on contiguous cells. Such osmotic pressure is essential to the physical environment of cellular material, and regulation of this pressure occurs by cell pumping of water into or out of the cell. Solutions delivered to the lungs that are isotonic normally do not create an imbalance in osmotic pressure in the lung fluid and therefore simply dilute the natural endogenous lung fluid with water and salt. Solutions of high osmotic content (i.e. hypertonic solutions) create an imbalance of osmotic pressure, with greater pressure in the lung fluid, causing cells to pump water into the lung fluid and therefore further dilute lung surfactant composition.

B. Active Ingredients

The formulations disclosed herein can be used by any route for delivery of a variety of molecules, especially antivirals and anti-infective molecules including antibiotics, antihistamines, bronchodilators, cough suppressants, anti-inflammatories, vaccines, adjuvants and expectorants. Examples of macromolecules include proteins and large peptides, polysaccharides and oligosaccharides, and DNA and RNA nucleic acid molecules and their analogs having therapeutic, prophylactic or diagnostic activities. Nucleic acid molecules include genes, antisense molecules that bind to complementary DNA to inhibit transcription, and ribozymes. Preferred agents are antiviral, steroid, bronchodilators, antibiotics, mucus production inhibitors and vaccines.

In the preferred embodiment, the concentration of the active agent ranges from about 0.01% to about 20% by weight. In a more preferred embodiment, the concentration of active agent ranges from between 0.9% to about 10%.

II. Carriers and Aerosols for Administration

Carriers can be divided into those for administration via solutions (liquid formulations) and those for administration via particles (dry powder formulations).

A. Liquid Formulations

Aerosols for the delivery of therapeutic agents to the respiratory tract have been developed. See, for example, Adjei, A. and Garren, *J. Pharm. Res.,* 7: 565-569 (1990); and Zanen, P. and Lamm, J.-W. *J. Int. J. Pharm.,* 114: 111-115 (1995). These are typically formed by atomizing the solution or suspension under pressure through a nebulizer or through the use of a metered dose inhaler ("MDI"). In the preferred embodiment, these are aqueous solutions or suspensions.

B. Dry Powder Formulations

The geometry of the airways is a major barrier for drug dispersal within the lungs. The lungs are designed to entrap particles of foreign matter that are breathed in, such as dust. There are three basic mechanisms of deposition: impaction, sedimentation, and Brownian motion (J. M. Padfield. 1987. In: D. Ganderton & T. Jones eds. Drug Delivery to the Respiratory Tract, Ellis Harwood, Chicherster, U.K.). Impaction occurs when particles are unable to stay within the air stream, particularly at airway branches. They are adsorbed onto the mucus layer covering bronchial walls and cleaned out by mucocilliary action. Impaction mostly occurs with particles over 5 μm in diameter. Smaller particles (<5 μm) can stay within the air stream and be transported deep into the lungs. Sedimentation often occurs in the lower respiratory system where airflow is slower. Very small particles (<0.6 μm) can deposit by Brownian motion. This regime is undesirable because deposition cannot be targeted to the alveoli (N. Worakul & J. R. Robinson. 2002. In: Polymeric Biomaterials, $2^{nd}$ ed. S. Dumitriu ed. Marcel Dekker: New York).

The preferred mean diameter for aerodynamically light particles for inhalation is at least about 5 microns, for example between about 5 and 30 microns, most preferably between 3 and 7 microns in diameter. The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different therapeutic agent may be administered to target different regions of the lung in one administration.

As used herein, the phrase "aerodynamically light particles" refers to particles having a mean or tap density less than about 0.4 g/cm$^3$. The tap density of particles of a dry powder may be obtained by the standard USP tap density measurement. Tap density is a standard measure of the envelope mass density. The envelope mass density of an isotropic particle is defined as the mass of the particle divided by the minimum sphere envelope volume in which it can be enclosed. Features contributing to low tap density include irregular surface texture and porous structure'.

Dry powder formulations ("DPFs") with large particle size have improved flowability characteristics, such as less aggregation (Visser, J., *Powder Technology* 58: 1-10 (1989)), easier aerosolization, and potentially less phagocytosis. Rudt, S. and R. H. Muller, *J. Controlled Release,* 22: 263-272 (1992); Tabata, Y., and Y. Ikada, *J. Biomed. Mater. Res.,* 22: 837-858 (1988). Dry powder aerosols for inhalation therapy are generally produced with mean diameters primarily in the range of less than 5 microns, although a preferred range is between one and ten microns in aerodynamic diameter. Ganderton, D., *J. Biopharmaceutical Sciences,* 3:101-105 (1992); Gonda, I. "Physico-Chemical Principles in Aerosol Delivery," in Topics in Pharmaceutical Sciences 1991, Crommelin, D. J. and K. K. Midha, Eds., Medpharm Scientific Publishers, Stuttgart, pp. 95-115 (1992). Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.,* 27: 769-783 (1996). Particles with degradation and release times ranging from seconds to months can be designed and fabricated by established methods in the art.

Particles can consist of the osmotic agent, alone, or in combination with drug, surfactant, polymer, or combinations thereof. Representative surfactants include L-alpha.-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty acids, sorbitan trioleate (Span 85), glycocholate, surfactin, poloxomers, sorbitan fatty acid esters, tyloxapol, phospholipids, and alkylated sugars. Polymers may be tailored to optimize particle characteristics including: i) interactions between the agent to be delivered and the polymer to provide stabilization of the agent and retention of activity upon delivery; ii) rate of polymer degradation and thus drug release profile; iii) surface characteristics and targeting capabilities via chemical modification; and iv) particle porosity. Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying the solution onto a substrate to form droplets of the desired size, and removing the solvent.

III. Administration of Formulations to the Respiratory Tract

A. Methods of Administration

The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. J. S. Patton & R. M. Platz. 1992. *Adv. Drug Del. Rev.* 8:179-196

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which lead to the ultimate respiratory zone, the alveoli or deep lung. The deep lung, or alveoli, is the primary target of inhaled therapeutic aerosols for systemic drug delivery.

The formulations are typically administered to an individual to deliver an effective amount to alter physical properties such as surface tension and viscosity of endogenous fluid in the upper airways, thereby enhancing delivery to the lungs and/or suppressing coughing and/or improving clearance from the lungs. Effectiveness can be measured using a system as described below. For example, saline can be administered in a volume of 1 gram to a normal adult. Exhalation of particles is then measured. Delivery is then optimized to minimize dose and particle number.

Formulations can be administered using a metered dose inhaler ("MDI"), a nebulizer, an aerosolizer, or using a dry powder inhaler. Suitable devices are commercially available and described in the literature.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6:273-313, 1990; and in Moren, "Aerosol dosage forms and formulations," in: Aerosols in Medicine, Principles, Diagnosis and Therapy, Moren, et al., Eds. Esevier, Amsterdam, 1985.

Delivery is achieved by one of several methods, for example, using a metered dose inhaler including HFA propellant, a metered dose inhaler with non-HFA propellant, a nebulizer, a pressurized can, or a continuous sprayer. For example, the patient can mix a dried powder of pre-suspended therapeutic with solvent and then nebulize it. It may be more appropriate to use a pre-nebulized solution, regulating the dosage administered and avoiding possible loss of suspension. After nebulization, it may be possible to pressurize the aerosol and have it administered through a metered dose inhaler (MDI). Nebulizers create a fine mist from a solution or suspension, which is inhaled by the patient. The devices described in U.S. Pat. No. 5,709,202 to Lloyd, et al., can be used. An MDI typically includes a pressurized canister having a meter valve, wherein the canister is filled with the solution or suspension and a propellant. The solvent itself may function as the propellant, or the composition may be combined with a propellant, such as FREON® (E.I. Du Pont De Nemours and Co. Corp.). The composition is a fine mist when released from the canister due to the release in pressure. The propellant and solvent may wholly or partially evaporate due to the decrease in pressure.

In an alternative embodiment, the formulation is in the form of salt or osmotically active material particles which are dispersed on or in an inert substrate, which is placed over the nose and/or mouth and the formulation particles inhaled. The inert substrate is preferably a biodegradable or disposable woven or non-woven fabric and more preferably the fabric is formed of a cellulosic-type material. An example is tissues currently sold which contain lotion to minimize irritation following frequent use. These formulations can be packaged and sold individually or in packages similar to tissue or baby wipe packages, which are easily adapted for use with a liquid solution or suspension.

Individuals to be treated include those at risk of infection, those with a viral or bacterial infection, allergy patients, asthma patients, and individuals working with immunocompromised patients or infected patients.

The formulation may be administered to humans or animals such as racehorses, breeding livestock, or endangered captive animals to protect these animals from infection by viral shedding. This may be accomplished by placing a nebulizer system near watering stations and triggering production of the aerosol as animals either approach or leave the station. Formulation may be sprayed over the animals as they walk through chutes or pens, or sprayed from spray trucks or even crop dusting type airplanes. Individual battery powered sprayers that are currently used to spray insecticides may be adapted for use in administering the solutions to the animal§ to minimize bioaerosol formation and/or dispersion.

The formulation may be administered to humans or animals at the onset of viral or bacterial outbreak to prevent spread of the disease to epidemic levels. Animals within a 10-kilometer radius of a FMD outbreak are currently deemed infected. These animals are subsequently slaughtered and disinfected. This aerosol system may be administered immediately to animals within this 10-kilometer radius zone and a further prescribed buffer zone outside this area to assure containment of the outbreak. The aerosol can then be administered for as long as is necessary to ensure success, i.e. beyond the normal period between first infection and symptom expression.

The formulation may be administered to humans or animals by creating an aqueous environment in which the humans and animals move or remain for sufficient periods of time to sufficiently hydrate the lungs. This atmosphere might be created by use of a nebulizer or even a humidifier.

Although described primarily with reference to pulmonary administration, it is understood that the formulations may be administered to individual animals or humans through inhalation; parenteral, oral, rectal, vaginal or topical administration; or by administration to the ocular space.

IV. Methods and Devices for Screening for "Over Producers"

A. Methods

Diagnosis of animals or humans who have an enhanced propensity to exhale aerosols (referred to herein as "over producers", "super-producers", or "superspreaders") can be done by screening for a number of factors including the measurement of expired air and inspired air, the assessment of exhaled particle numbers, the assessment of exhaled particle size, the assessment of tidal volume and respiratory frequency during sampling, and the assessment of viral and bacterial infectivity. The assessment of exhaled particle numbers is done at a respiratory flow rate of about 10 to about 120 liters per minutes (LPM).

B. Devices

A device with sufficient sensitivity to accurately count sub-micron sized particles was designed and assembled as described in the examples. Preferably the device is portable and operates on batteries. The measurement of particle number and particle size can be done by infrared spectroscopy, laser diffraction, or light scattering In Vitro Testing of Bioaerosol Transmission The following in vitro method can be used to test the effectiveness of delivering saline or other solutions of an osmotically active material on bioaerosol generation in the airways. A "cough machine" (M. King, J. M. Zahm, D. Pierrot, S. Vaquez-Girod, E. Puchelle. *Biorheology.* (1989) 26:737-745) is used to control air speed experienced by simulated mucus lining of the airway. Labeled nanoparticles can be incorporated into the fluid, and a filter placed at the exit of the cough machine to collect the aerosol droplets generated. A variety of compounds can be added to alter shear viscosity, elongational viscosity, and surface tension. The test is repeated at varying air velocities, below, including, and above 25 m/s.

Toxicity Studies

Compounds to be administered can be tested for non-toxicity. For example, preliminary in vitro studies can be conducted to test the toxicity of solutions upon addition to monolayers of fibroblast cells. NIH 3T3 fibroblasts are plated onto glass Lab-Tek™ coverslip chambers (NUNC, Rochester, N.Y.) and grown to confluence. The cells are then exposed to a solution in 10% FBS DMEM for 10 seconds and returned to the incubator after several washes with 10% FBS in DMEM. After 15 minutes the cells are exposed to 10 µM Cell-Tracker™ Green CMFDA (Molecular Probes, Eugene, Oreg.) for 30 min. The cells are then washed several times with 10% FBS DMEM and placed in a 37° C., 5% $CO_2$ microscope chamber. The CMFDA stain readily enters the cell and if the cell is alive, the stain becomes enzymatically modified and cannot leave. Thus viable cells will fluoresce brightly while dead cells will not. The cells are imaged with an inverted fluorescence microscope.

In vivo toxicity studies determine which of the most effective formulations of the in vitro studies are the least toxic. Animals will be administered the prepared formulations and intravenous blood samples will be collected. Also, tracheal lavage will provide information about damage to lung tissue resulting from administration of the preparations.

Treatment is continued for as long as there is risk of infection or spread of disease, with treatment repeated as necessary to prevent or limit viral shedding. In the case of asthma, allergy and other pulmonary disorders, treatment will be continued to maintain the desired pulmonary parameters.

The present invention will be further understood by reference to the following non-limiting examples.

EXAMPLES

Example 1

In Vitro Simulation

As shown in FIG. 1, a simulated cough machine system was designed similar to that described by King Am. J. Respir. Crit. Care Med. 156(1):173-7 (1997). An air-tight 6.25-liter Plexiglas tank equipped with a digital pressure gauge and pressure relief valve was constructed to serve as the capacitance function of the lungs. To pressurize the tank, a grade dry compressed air cylinder with regulator was connected to the inlet. At the outlet of the tank, an Asco two-way normally-closed solenoid valve (8210G94) with a sufficient Cv flow factor was connected for gas release. The solenoid valve was wired using a typical 120V, 60 Hz light switch. Connected to the outflow of the solenoid valve was a Fleisch no. 4 pneumotachograph, which created a Poiseuille flow needed to examine the "cough" profile. The outlet of the Fleisch tube was connected to a ¼" NPT entrance to our model trachea. A Validyne DP45-14 differential pressure transducer measured the pressure drop through the Fleisch tube. A Validyne CD 15 sine wave carrier demodulator was used to amplify this signal to the data acquisition software. Weak polymeric gels with rheological properties similar to tracheobronchial mucus were prepared as described by King et al Nurs Res. 31(6): 324-9 (1982). Locust bean gum (LBG) (Fluka BioChemika) solutions were crosslinked with sodium tetraborate ($Na_2B_4O_7$) (J. T. Baker). LBG at 2% wt/vol was dissolved in boiling Milli-Q distilled water. A concentrated sodium tetraborate solution was prepared in Milli-Q distilled water. After the LBG solution cooled to room temperature, small amounts of sodium tetraborate solution were added and the mixture was slowly rotated for 1 minute. The still watery mucus simulant was then pipetted onto the model trachea creating simulant depth based on simple trough geometry. Mucus simulant layers were allowed 30 minutes to crosslink prior to initiation of "cough" experiments. At this point, t=0 min, time points were measured, followed by t=30 min and t=60 min. Final concentrations of sodium tetraborate ranged from 1-3 mM. An acrylic model trachea was designed 30 cm long with interior width and height of 1.6 cm. The model trachea formed a rectangular shaped tube with a separate top to fit, allowing for easy access to the mucus simulant layer. A gasket and C-clamps were used to create an air-tight seal. A rectangular cross-section was chosen to enable uniform mucus simulant height and to avoid problems associated with round tubes and gravity drainage. The cross-sectional area of the model trachea was also physiologically relevant. The end of the model trachea remained open to the atmosphere. Nebulized solutions were delivered to the mucus simulant via a PARI LC Jet nebulizer and Proneb Ultra compressor. Formulations included normal isotonic 0.9% saline (VWR) and 100 mg/mL of synthetic phospholipids 1,2-Dipalmitoyl-sn-glycero-3-phosphocholine/1-Palmitoyl-2-oleoyl-sn-glycero-3-phosphoglycerol (DPPC/POPG) (Genzyme) 7/3 wt % suspended in isotonic saline. 3 mL of the chosen formulation was pipetted into the nebulizer and aerosolized until nebulizer sputter through the open-ended but clamped model trachea trough on the layer of mucus simulant. The model trachea was then attached to the outlet of the Fleisch tube prior to t=0 min experiments. As well, t=30 min and t=60 min (post-dose) experiments were performed.

A Sympatec HELOS/KF laser diffraction particle sizer was used to size the created mucus simulant bioaerosols. The Fraunhoffer method for sizing diffracted particles was used. The HELOS was equipped with an R2 submicron window module enabling a measuring range of 0.25-87.5 µm. Prior to "cough" experiments, the end of the model trachea was, adjusted to be no more than 3 cms from the laser beam. As well, the bottom of the model trachea was aligned with the 2.2 mm laser beam using support jacks and levels. Dispersed bioaerosols were collected after passing through the diffraction beam using a vacuum connected to an inertial cyclone followed by a HEPA filter. Before each run, the laser was referenced for 5 s to ambient conditions. Measurement began after a specified trigger condition of optical concentration ($C_{opt}$)>0.2% and stopped 2 s after $C_{opt} \leq 0.2\%$. Sympatec WINDOX software was used to create cumulative and density distribution graphs versus log particle size by volume.

A typical cough profile, consisting of a biphasic burst of air, was passed over the 1.5 mm layer of mucus simulant. The initial flow or air possessed a flow rate of about 12 L/s for 30-50 ms. The second phase lasted 200-500 ms and then rapidly decayed. A representative actual cough profile is compared with a simulated cough profile (5 psi tank pressure) in FIG. 2.

Bioaerosol particle concentration following three coughs was measured over time (FIG. 3) in the case of an undisturbed mucus simulant, and in the cases of saline delivery (FIG. 3) and surfactant delivery (not shown). In the undisturbed case, bioaerosol particle size remains constant over time with a median size of about 400 nanometers. Following the addition of saline, bioaerosol particle size increases from 1 micron (t=0) to about 60 microns (t=30 min) and then diminishes to 30 microns (t=60 min).

These in vitro results show that saline delivered to a mucus layer causes a substantial increase in particle size on breakup, possibly owing to an increase in surface tension. As indicated by the in vivo results, the larger size droplets are less capable of exiting the mouth. Therefore, delivery of the solution serves to significantly lower the number of expired particles.

Example 2

Reduction of Exhaled Aerosol Particles in Human Study

A proof of concept study of exhaled aerosol particle production was performed using 12 healthy subjects. The objectives of the study were (1) to determine the nature of exhaled bioaerosol particles (size distribution and number); (2) to validate the utility of a device that is sensitive enough to accurately count the exhaled particles; (3) to assess the baseline count of particles exhaled from the healthy lung; and (4) to measure the effect of two exogenously administered treatment aerosols on exhaled particle count suppression. Experiments were performed with different particle detectors to determine average particles per liter and average particle size for healthy human subjects. Following the inspiration of particle-free air, healthy subjects breathe out as little as 1-5 particles per liter, with an average size of 200-400 nm in diameter. Significant variations occur in numbers of particles from subject to subject, so that some subjects exhale as many as 30,000 particles per liter, again predominantly of submicron particle size. A device with sufficient sensitivity to accurately count sub-micron sized particles was designed and assembled. The LASER component of the device was calibrated in accordance with manufacturer procedures (Climet Instruments Company, Redlands, Calif.). This device accurately measured particles in the range of 150-500 nm with a sensitivity of 1 particle/liter. A series of filters eliminated all background particle noise.

Following protocol IRB approval, 12 healthy subjects were enrolled in the study. Inclusion criteria were good health, age 18-65 years, normal lung function ($FEV_1$ predicted>80%), informed consent and capability to perform the measurements. Exclusion criteria were presence or a history of significant pulmonary disease (e.g. asthma, COPD, cystic fibrosis), cardiovascular disease, acute or chronic infection of the respiratory tract, and pregnant or lactating females. One individual was not able to complete the entire dosing regimen and therefore was excluded from the data analysis.

Following a complete physical exam, the subjects were randomized into two groups: those to initially receive prototype formulation 1 and those to receive prototype formulation 2. Baseline exhaled particle production was measured after a two minute "wash out" period on the device. The assessment was made over a two minute period with the per-minute count derived from the average of the two minutes. Following the baseline measurement, the prototype formulation was administered over a six minute period using a commercial aqueous nebulizer (Pari Respiratory Equipment, Starnberg, Germany). Formulation 1 consisted of an isotonic saline solution. Formulation 2 consisted of a combination of phospholipids suspended in an isotonic saline vehicle. Following administration, exhaled particle counts were assessed 5 minutes, 30 minutes, one hour, two hours, and three hours after the single administration.

Figure 4A:
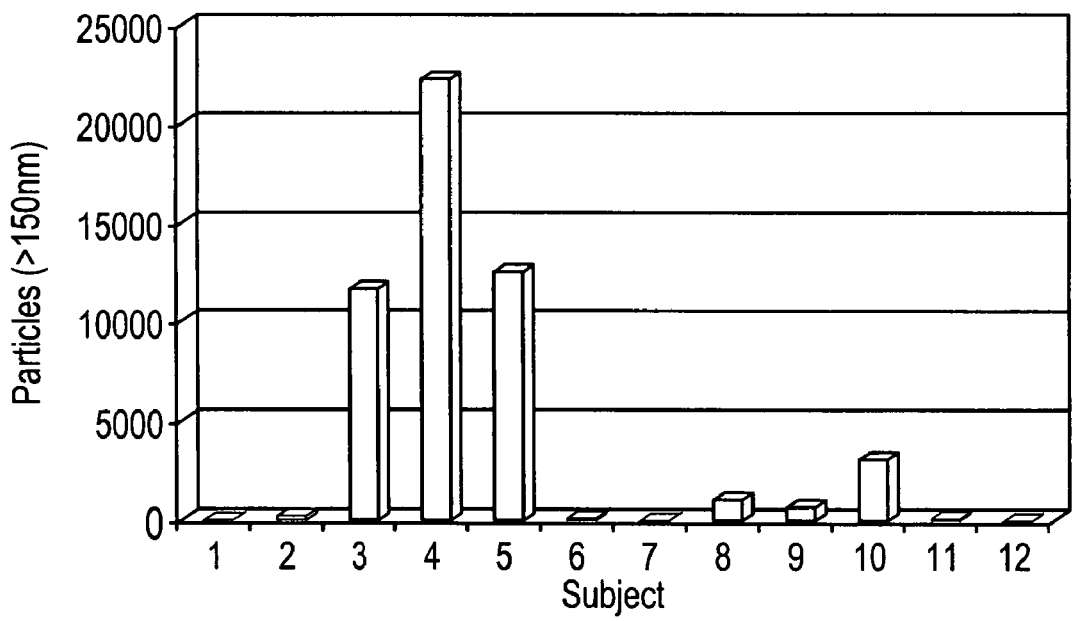
FIG. 4A is a chart of baseline particle count (greater than 150 nm) expired by individuals (n=11) while inhaling particle free air.
Figure 4B:
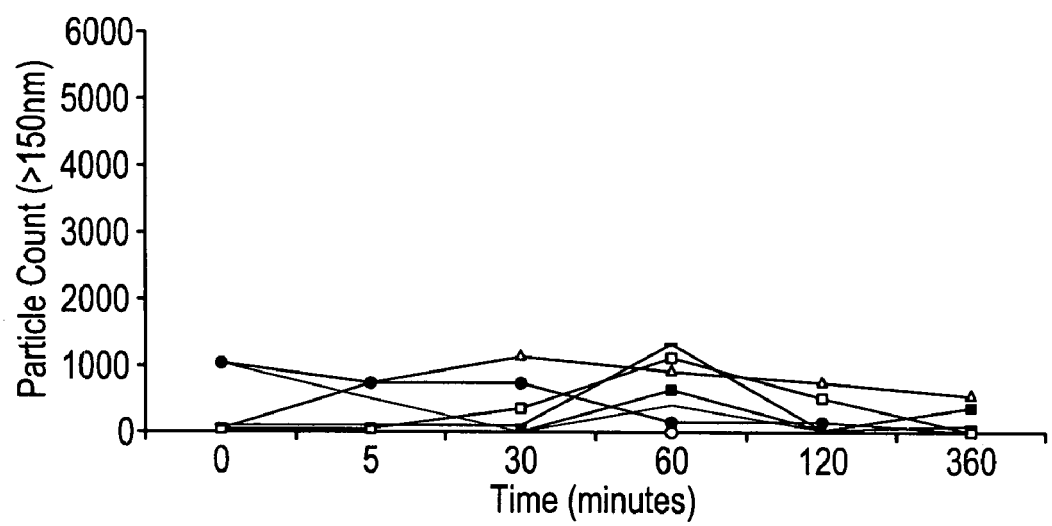
FIG. 4B is a graph of particle count (greater than 150 nm) expired by individuals (n=11) after saline (approximately 1 g) had been administered to the lungs in the form of an aerosol over time (minutes).

As shown in FIG. 4A, substantial inter-subject variability was found in baseline particle counts. The data shown are measurements made prior to administration of one of the test aerosols. This baseline expired particle result points to the existence of "super producers" of exhaled aerosols. In this study "super-producers" were defined as subjects exhaling more than 1,000 particles/liter at baseline measurement. FIG. 4B shows the individual particle counts for subjects receiving Formulation 1. The data indicate that a simple formulation of exogenously applied aerosol can suppress exhaled particle counts.

Figure 5A:
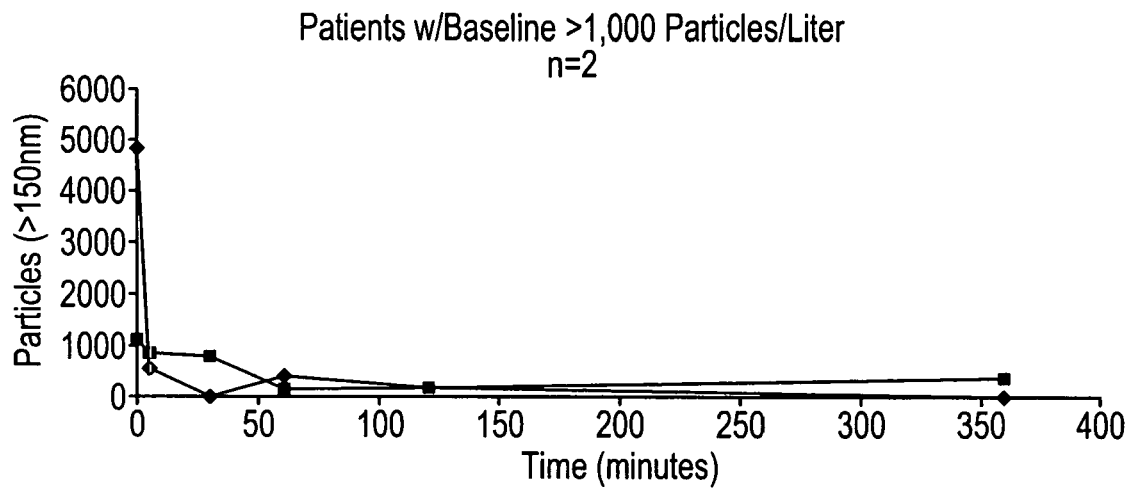
FIG. 5A is a graph of particle count (greater than 150 nm) exhaled by individuals (n=2) who, prior to treatment have a baseline exhalation of greater than 1000 particles/liter (while inhaling particle free air), after isotonic saline solution (approximately 1 g solution) had been administered to the lungs in the form of an aerosol over time (minutes)

FIG. 5A shows the effect of prototype formulation 1 on the two "super-producers" found at baseline in this group. These data indicate that the prototype formulation may exert a more pronounced effect on super-producers.

Figure 5B:
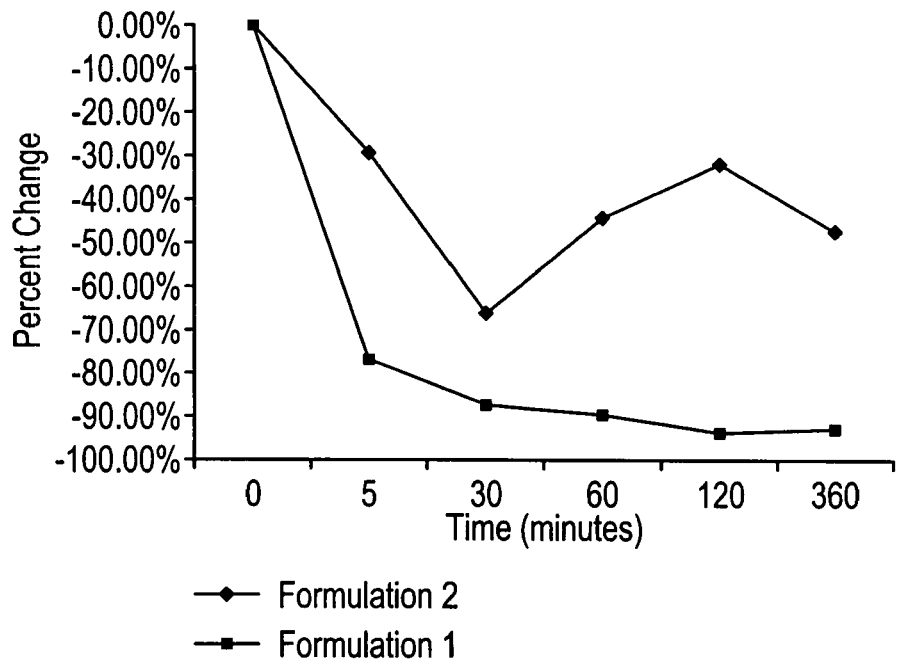
FIG. 5B is a graph of percent change (versus baseline) of the cumulative exhaled particle counts over time (minutes).

Similar results were found on delivery of formulation 2. FIG. 5B summarizes the percent change (versus baseline) of the cumulative exhaled particle counts for the "super-producers" identified in the two treatment groups. Results from this study demonstrate that exhaled particles can be accurately measured using a laser-detection system, that these particles are predominantly less than 1 micron in diameter, and that the number of these particles varies substantially from subject to subject. "Super-producing" subjects respond most markedly to delivery of an aerosol that modifies the physical properties of the surface of the lining fluid of the lungs. Such super-producers might bear significant responsibility for pathogen shedding and transmission in a population of infected patients. These data also demonstrate that suppressing aerosol exhalation is practical with relatively simple and safe exogenously administered aerosol formulations.

Example 3

Large Animal Study

Seven (7) Holstein bull calves were anesthetized, intubated, and screened for baseline particle exhalation by optical laser counting. Animals were subsequently untreated (sham) or treated with a nebulized aerosol of saline at one of three doses (1.8 minutes, 6.0 minutes or 12.0 minutes). During the sham dosage, the animals were handled in the same manner as they were when the dosages of the isotonic saline solution were administered. One animal was dosed per day and nebulizer doses were randomized throughout the exposure period (see Table 1 for dosing schedule). Each animal was slated to receive all doses during the duration of the study. Following the administration of each dose, exhaled particle counts were monitored at discrete timepoints (0, 15, 30, 45, 60, 90, 120) through 180 minutes.

The exposure matrix for the animals included in the study is found in Table 1. The dosing occurred over a 57 day period, with at least a 7 day interval between dosages. Each animal (n=7) received each dose at least once during the duration of dosing, with the exception of the omission of one 6.0 minute dose (see animal no. 1736) and one 12.0 minute dose (see animal no. 1735). These two were excluded due to unexpected problems with the ventilator and/or anesthesia equipment.

TABLE 1

Dosing Regime for Large Animals

| Animal No. | Sham | Dosage 1.8 min. | Dosage 6.0 min. | Dosage 12.0 min. |
|---|---|---|---|---|
| 1731 | Day 17 | Day 3 | Day 10 | Day 25 |
| 1732 | Day 7 | Day 21 | Day 1 | Day 14 |
| 1735 | Day 18 | Day 11 | Day 4 | N/A |
| 1736 | Day 23 | Day 2 | N/A | Day 9 |
| 1738 | Day 8 | Day 15 | Day 36 | Day 25 |
| 1739 | Day 20 | Day 38 | Day 30 | Day 45 |
| 1741 | Day 50 | Day 35 | Day 57 | Day 42 |

Results

Figure 6A:
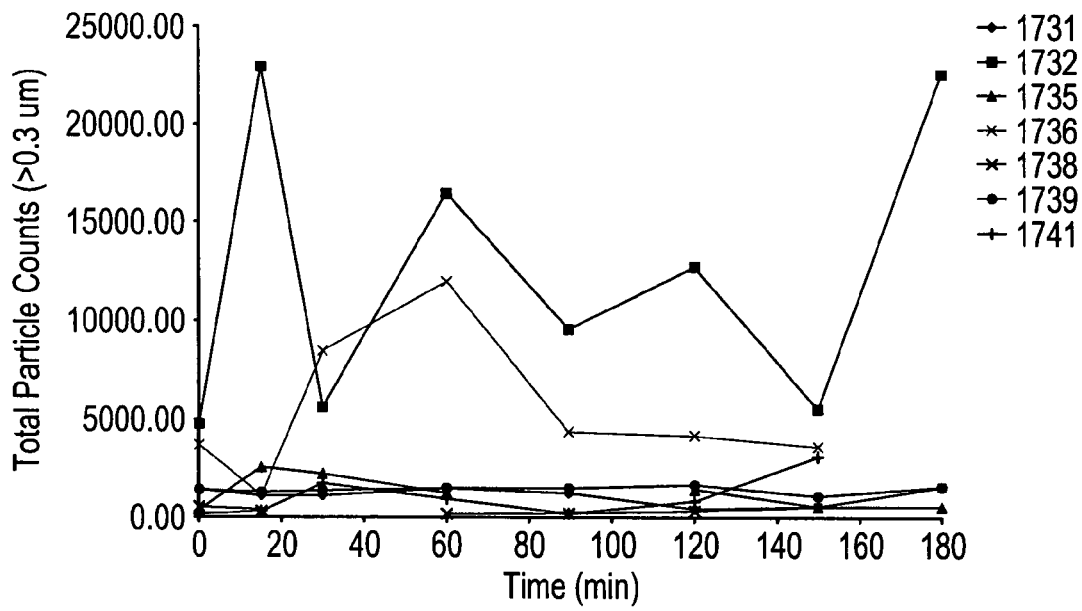
FIG. 6A is a graph of total particles exhaled (greater than 0.3 microns) over time (minutes) showing data obtained from sham treated animals.

FIG. 6A show the particle count over time for each animal after it received a sham dosage. Each timepoint typically represents the mean of at least three particle count determinations. The data in FIG. 6A shows that certain individual animals inherently produce more particles than others ("superspreaders"). Additionally, the data show that throughout the assessment period, quiescently breathing anesthetized animals maintain a relatively stable exhaled particle output (see e.g. Animal nos. 1731, 1735, 1738, 1739, and 1741).

Figure 6B:
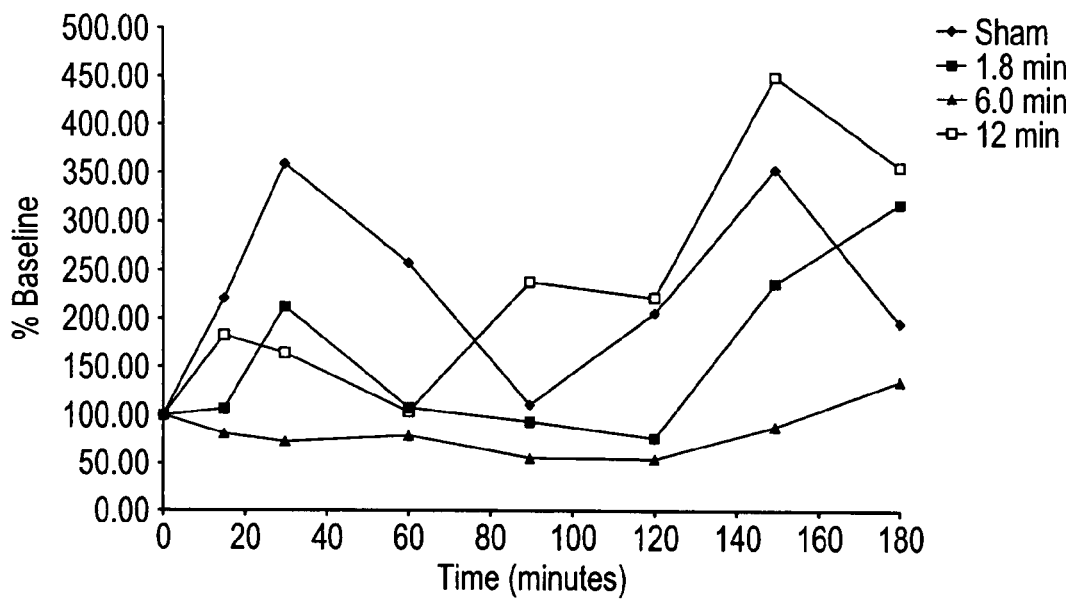
FIG. 6B is a graph of mean percent (%) baseline particle counts over time (minutes) showing data obtained from animals treated with nebulized saline for 1.8 minutes (-■-) 6.0 minutes (-▲-), 12.0 minutes (-□-), and sham (-♦-).

FIG. 6B represents the mean percent change in exhaled particle counts over time following each treatment. Each data point represents the mean of six to seven measurements from the treatment group. All animals had returned to baseline by 180 minutes post treatment. The data suggest that the 6.0 minute treatment period provides an adequate dose to prevent the exhalation of particles for at least 150 minutes post-treatment. The other treatments appear to be either too short or too long to provide an effective, lasting suppression of aerosol exhalation.

CONCLUSION

The study conducted in cattle demonstrates the efficacy of isotonic saline on the formation of exhaled aerosols in spontaneously breathing animals relevant to livestock herds. Based on the results, delivery of isotonic saline can markedly diminish the number of expired aerosol particles in a dose-responsive manner. In addition, this large animal dosing system allows for repeated controlled exposures. By using each animal as its own control via the daily pre-exposure baseline and the sham exposure, the inherent variability associated with particle exhalation can be understood. The data suggests that 6.0 minutes of saline nebulization diminishes particle exhalation for a minimum of 120 minutes in cows.

We claim:

1. A method for reducing the exhalation of pulmonary infection particles in a subject having a pulmonary infection comprising administering to the subject a therapeutically effective amount of a non-surfactant aerosol formulation comprising an active agent and a pharmaceutically acceptable diluent, said diluent containing greater than 0.9% to 5% (w/w) NaCl, thereby reducing exhalation of particles in said subject, with the proviso that said active agent is not a bronchodilator.

2. The method of claim 1, wherein the active agent is selected from the group consisting of an antibiotic, an antihistamine, and an antiviral agent.

3. The method of claim 1, wherein the pulmonary infection particles are between 80 to 120 nm in diameter.

4. The method of claim 1, wherein the pulmonary infection particles are greater than about 120 nm in diameter.

5. The method of claim 1, wherein the subject is human.

6. The method of claim 1, wherein the pulmonary infection is selected from the group consisting of tuberculosis, SARS, influenza, cytomegalovirus, respiratory syncytial virus, African swine fever, coronavirus, rhinovirus, tularemia, bubonic plague, anthrax and foot and mouth disease.

7. The method of claim 1, wherein the pulmonary infection is influenza.

8. The method of claim 1, wherein the non-surfactant aerosol formulation is administered in an amount effective to dilute endogenous airway lining fluid, to dilute endogenous surfactant fluid, to alter surface tension of endogenous surfactant fluid, to alter surface elasticity of endogenous surfactant fluid, to alter surface viscosity of endogenous airway lining fluid in the subject or to alter bulk viscosity of endogenous airway lining fluid in the subject.

9. The method of claim 1, wherein the non-surfactant aerosol formulation is an aqueous solution.

10. The method of claim 1, wherein the non-surfactant aerosol formulation is in the form of a suspension.

11. The method of claim 1, wherein the non-surfactant aerosol formulation is in the form of a dry powder.

12. The method of claim 1, wherein the pulmonary infection is a tuberculosis infection.

13. The method of claim 1, wherein the pulmonary infection is a coronavirus infection.

14. The method of claim 1, wherein the pulmonary infection is a SARS infection.

15. The method of claim 1, wherein the pulmonary infection is a cytomegalovirus infection.

16. The method of claim 1, wherein the pulmonary infection is a respiratory syncytial virus infection.

17. The method of claim 1, wherein the pulmonary infection is a rhinovirus infection.

18. The method of claim 1, wherein the pulmonary infection is an infection that causes bronchiolitis.

19. The method of claim 1, wherein the pulmonary infection is an anthrax infection.

20. A method of decreasing exhalation of particles in an individual comprising administering to the individual an effective amount of a biocompatible formulation comprising a solution that comprises isotonic saline and an osmotically active material in an amount from 0.9% to about 10% concentration by weight, wherein the formulation is administered in an amount effective to decrease exhalation of particles in said individual, with the proviso that said osmotically active material is not a bronchodilator.

21. The method of claim 20, wherein said individual has a respiratory disease.

22. The method of claim 21, wherein the respiratory disease is selected from the group consisting of allergy, asthma, chronic bronchitis, emphysema, acute respiratory distress syndrome, tuberculosis, SARS, influenza, cytomegalovirus, respiratory syncytial virus, African swine fever, coronavirus, rhinovirus, tularemia, bubonic plague, anthrax, bronchiolitis and foot and mouth disease.

23. The method of claim 20, wherein said osmotically active material is selected from the group consisting of a salt and a sugar.

24. The method of claim 23, wherein said osmotically active material is a sugar.

25. The method of claim 24, wherein said osmotically active material is mannitol.

26. The method of claim 23, wherein said osmotically active material is a salt.

27. The method of claim 26, wherein said osmotically active material is a binary salt.

28. The method of claim 20, wherein said formulation further comprises an active agent.

29. The method of claim 20, wherein said active agent is selected from the group consisting of an antibiotic, an antihistamine, and an antiviral agent.

30. The method of claim 20, wherein the formulation creates a coating on the respiratory tract lining fluid.

31. The method of claim 20, wherein said formulation contains 0.9% (w/w) NaCl.

32. The method of claim 20, wherein said formulation is administered to the individual as an aerosol.

33. The method of claim 20, wherein said formulation is administered to the individual by a nebulizer.

34. A method for reducing the exhalation of pulmonary infection particles in a subject having a pulmonary infection comprising administering to the subject a therapeutically effective amount of a non-surfactant aerosol formulation comprising saline and an active agent, wherein said formulation is hypertonic and with the proviso that said active agent is not a bronchodilator, thereby reducing exhalation of particles in said subject.

35. A method for treating a respiratory disease selected from the group consisting of allergy, tuberculosis, SARS, influenza, cytomegalovirus, respiratory syncytial virus, African swine fever, coronavirus, rhinovirus, tularemia, bubonic plague, anthrax, bronchiolitis and foot and mouth disease in an individual having said respiratory disease comprising administering a therapeutically effective amount of a non-surfactant aerosol formulation comprising saline and an active agent to said individual, wherein said formulation is hypertonic and with the proviso that said active agent is not a bronchodilator.

36. The method of claim 35, wherein said formulation creates a coating on the respiratory tract lining fluid.

37. The method of claim 35, wherein said formulation is administered to the individual by a nebulizer.

38. The method of claim 35, wherein said active agent is selected from the group consisting of an antibiotic, an antihistamine, a corticosteroid and an antiviral agent.

39. A method for treating a respiratory disease selected from the group consisting of allergy, tuberculosis, SARS, influenza, cytomegalovirus, respiratory syncytial virus, African swine fever, coronavirus, rhinovirus, tularemia, bubonic plague, anthrax, bronchiolitis and foot and mouth disease in an individual having said respiratory disease comprising administering a therapeutically effective amount of a non-surfactant aerosol formulation comprising an osmotically active material, the osmotically active material present at greater than 0.9% to about 10% by weight, to said individual, wherein said formulation is hypertonic and with the proviso that said osmotically active material is not a bronchodilator.

40. A method for reducing the exhalation of pulmonary infection particles in a subject having a pulmonary infection comprising administering to the subject a therapeutically effective amount of a non-surfactant aerosol formulation consisting essentially of an active agent and a pharmaceutically acceptable diluent, said diluent containing greater than 0.9% to 5% (w/w) NaCl and said active agent selected from the group consisting of an antibiotic, an antihistamine, a corticosteroid and an antiviral agent, thereby reducing exhalation of particles in said subject.

41. A method of decreasing exhalation of particles in an individual comprising administering to the individual an effective amount of a biocompatible formulation comprising solution that consists essentially of isotonic saline and an osmotically active material in an amount from 0.9% to about 10% concentration by weight, wherein the formulation is administered in an amount effective to decrease exhalation of particles in said individual.

42. A method for treating a respiratory disease selected from the group consisting of allergy, tuberculosis, SARS, influenza, cytomegalovirus, respiratory syncytial virus, African swine fever, coronavirus, rhinovirus, tularemia, bubonic plague, anthrax, bronchiolitis and foot and mouth disease in an individual having said respiratory disease comprising administering a therapeutically effective amount of a non-surfactant aerosol formulation consisting essentially of a hypertonic saline formulation containing an active agent to said individual, wherein said active agent is selected from the group consisting of an antibiotic, an antihistamine, a corticosteroid and an antiviral agent.

43. A method for reducing the exhalation of pulmonary infection particles in a subject having a pulmonary infection comprising administering to the subject a therapeutically effective amount of a non-surfactant aerosol formulation consisting essentially of saline and an active agent, wherein said formulation is hypertonic and wherein said active agent is selected from the group consisting of an antibiotic, an antihistamine, a corticosteroid and an antiviral agent, thereby reducing exhalation of particles in said subject.

\* \* \* \* \*